US009186197B2

(12) United States Patent
McKay

(10) Patent No.: US 9,186,197 B2
(45) Date of Patent: Nov. 17, 2015

(54) NERVE AND SOFT TISSUE ABLATION DEVICE FOR TREATING PAIN

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 287 days.

(21) Appl. No.: 13/835,557

(22) Filed: Mar. 15, 2013

(65) Prior Publication Data
US 2014/0276703 A1    Sep. 18, 2014

(51) Int. Cl.
  *A61B 18/02* (2006.01)
  *A61B 18/00* (2006.01)
  *A61B 19/00* (2006.01)

(52) U.S. Cl.
CPC ........ *A61B 18/02* (2013.01); *A61B 2018/00351* (2013.01); *A61B 2018/00434* (2013.01); *A61B 2018/00529* (2013.01); *A61B 2018/00541* (2013.01); *A61B 2018/00565* (2013.01); *A61B 2018/00577* (2013.01); *A61B 2018/00821* (2013.01); *A61B 2018/00875* (2013.01); *A61B 2018/00886* (2013.01); *A61B 2018/0262* (2013.01); *A61B 2018/0293* (2013.01); *A61B 2019/462* (2013.01); *A61B 2019/464* (2013.01); *A61B 2019/5251* (2013.01); *A61B 2019/5255* (2013.01)

(58) Field of Classification Search
CPC ........... A61B 18/02; A61B 2018/0212; A61B 2018/0262; A61B 2018/0287; A61B 2018/00351; A61B 2018/00434; A61B 2018/00529

USPC ...................................................... 606/21–25
See application file for complete search history.

(56) References Cited

U.S. PATENT DOCUMENTS

| 5,147,355 A | 9/1992 | Friedman et al. |
| 5,334,181 A | 8/1994 | Rubinsky et al. |
| 5,520,682 A | 5/1996 | Baust et al. |
| 5,906,612 A | 5/1999 | Chinn |
| 6,032,675 A | 3/2000 | Rubinsky |
| 6,179,831 B1 | 1/2001 | Bliweis |
| 6,190,378 B1 | 2/2001 | Jarvinen |
| 6,485,422 B1 | 11/2002 | Mikus et al. |
| 6,579,287 B2 | 6/2003 | Wittenberger et al. |
| 6,672,095 B1 | 1/2004 | Luo |
| 6,761,715 B2 | 7/2004 | Carroll |
| 6,789,545 B2 | 9/2004 | Littrup et al. |

(Continued)

FOREIGN PATENT DOCUMENTS

WO    2010102310 A2    9/2010

*Primary Examiner* — Christopher D Koharski
*Assistant Examiner* — Michael Carey
(74) *Attorney, Agent, or Firm* — Sorell Lenna & Schmidt LLP

(57) ABSTRACT

Ablation kits useful for destroying nerve and soft tissue via a minimally invasive procedure to alleviate pain are provided. The device comprises a probe having an exterior and an interior. The exterior comprises a tip and the interior defines a passage having a filament and insulation disposed therein. The filament has an opening configured to release a pressurized material into the interior of the probe so as to cool the tip to a selected temperature to ablate nerve and/or soft tissue. A bone piercing instrument is provided that is configured to pierce bone so as to allow entry of the probe into the bone. Methods for ablating nerve and/or soft tissue utilizing the ablation devices are also provided.

20 Claims, 5 Drawing Sheets

(56) References Cited

U.S. PATENT DOCUMENTS

| | | |
|---|---|---|
| 6,796,979 B2 | 9/2004 | Lentz |
| 6,902,547 B2 | 6/2005 | Aves et al. |
| 6,926,711 B2 | 8/2005 | Lentz et al. |
| 7,381,208 B2 | 6/2008 | Van der Walt et al. |
| 7,510,554 B2 | 3/2009 | Duong et al. |
| 7,625,368 B2 | 12/2009 | Schechter et al. |
| 7,641,679 B2 | 1/2010 | Joye et al. |
| 7,846,154 B2 | 12/2010 | Bliweis et al. |
| 7,938,822 B1 | 5/2011 | Berzak et al. |
| 7,967,814 B2 | 6/2011 | Levin |
| 7,967,815 B1 | 6/2011 | Berzak et al. |
| 8,083,733 B2 | 12/2011 | Toubia et al. |
| 8,162,812 B2 | 4/2012 | Shai et al. |
| 2002/0068964 A1 | 6/2002 | Dobak |
| 2004/0049177 A1 | 3/2004 | Zvuloni et al. |
| 2005/0177215 A1 | 8/2005 | Rosenberg |
| 2005/0192564 A1* | 9/2005 | Cosman et al. ............... 606/21 |
| 2005/0240239 A1 | 10/2005 | Boveja et al. |
| 2007/0156125 A1 | 7/2007 | DeLonzor |
| 2007/0191732 A1 | 8/2007 | Voegele |
| 2008/0306475 A1 | 12/2008 | Lentz et al. |
| 2009/0036823 A1 | 2/2009 | LePivert |
| 2009/0192505 A1 | 7/2009 | Askew et al. |
| 2009/0299357 A1 | 12/2009 | Zhou |
| 2010/0168739 A1 | 7/2010 | Wu et al. |
| 2010/0179527 A1 | 7/2010 | Watson et al. |
| 2010/0292764 A1 | 11/2010 | Soomro et al. |
| 2011/0270238 A1 | 11/2011 | Rizq et al. |
| 2011/0313411 A1 | 12/2011 | Anderson et al. |
| 2012/0046531 A1 | 2/2012 | Hua |
| 2012/0065630 A1 | 3/2012 | Berzak et al. |
| 2012/0089047 A1 | 4/2012 | Ryba et al. |
| 2012/0109116 A1 | 5/2012 | Asconeguy et al. |
| 2012/0253336 A1 | 10/2012 | Littrup et al. |

* cited by examiner

US 9,186,197 B2

NERVE AND SOFT TISSUE ABLATION DEVICE FOR TREATING PAIN

FIELD

The present invention relates generally to devices and methods for ablating nerve and/or soft tissue. More specifically, the devices and methods are useful for ablating nerve and/or soft tissue via a minimally invasive procedure to alleviate pain.

BACKGROUND

Acute and chronic pain management has been a concern for as long as medicine has been practiced. Several methods of inducing analgesia and anesthesia have been developed. For example, the use of chemical substances is perhaps the most common approach to pain relief which requires suitable substances that are effective, safe to humans, and do not cause complications or abnormal reactions. Despite the great advances that have been made in the field of anesthesiology, and in the field of pain relief in general, there are still some drawbacks to chemical-based approaches. For instance, the anesthetics generally available today must be administered in carefully graduated doses to assure the patient's well being, require extended periods of fasting prior to treatment, and are often accompanied by undesirable after effects such as nausea.

One alternative approach that is commonly used for providing pain relief is ablation in which nerves and/or tissue is removed and/or destroyed. Two approaches to destroying tissue via ablation are through cold or hot ablation procedures and techniques. Various categories of ablation include but are not limited to electrical, radiation, light, radiofrequency, ultrasound, cryotherapy, thermal, microwave and hydromechanical. One form of hot ablation is radiofrequency ablation. During radiofrequency (RF) ablation, current passing through tissue from the active electrode leads to ion agitation, which is converted by means of friction into heat. The process of cellular heating includes almost immediate and irreparable cellular damage, which leads to coagulation necrosis. Because ion agitation, and thus tissue heating, is greatest in areas of highest current density (e.g., closest to the active electrode tip), necrosis is limited to a relatively small volume of tissue surrounding the RF electrode.

Another form of ablation uses cold ablation and is called cryoablation. During cryoablation, tissue is frozen or rapid freeze/thaw cycles are inflicted upon the tissue. There are many advantages to using cryoablation instead of radiofrequency ablation. For example, cryoablation is safer especially near critical vasculature and there is less risk of post-procedure neuritis or neuromas following neuroablation for the treatment of pain.

The current procedures and techniques using cryoablation used destroy tissue due to rupturing of cells and/or cell organelles within the tissue. Deep tissue freezing is affected by insertion of a tip of a cryosurgical device into the tissue, either transperineally, endoscopically or laproscopically, and a formation of, what is known in the art as, an ice ball around the tip. During freezing, ice formation within the extracellular space creates an osmotic gradient, resulting in cellular dehydration. Ice crystals then form within the cells causing cell membranes to rupture resulting in cell death.

In addition, when the adjacent tissues are present at opposite borders with respect to the freeze treated tissue and since the growth of the ice ball is in a substantially similar rate in all directions toward its periphery, if otherwise, the ice ball reaches one of the borders before it reaches the other border, and decision making must be made on whether to continue the process of freezing, risking damage to close healthy tissues, or to halt the process of freezing, risking a non-complete destruction of the treated tissue.

Traditional cryoablation systems can provide removal capabilities of soft tissue via the application of single needles that form an ice ball centered around a tip, but the procedures can take a considerable amount of time to perform because the ice balls are directly attached to the needle tips and a medical practitioner must wait for the ice balls to melt enough in order to remove the needles from the site.

Sometimes, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Accordingly, there is a need for devices and methods to provide efficient destruction of nerve and/or soft tissue by cryoablation utilizing a device that allows a medical practitioner to accurately and optimally position the components of the device at various locations, such as, for example, multiple facet joints and/or multiple spinal levels such that the medical practitioner can quickly move the device from one location to the next. Moreover, a device is needed for use during a minimally invasive procedure and/or during an open surgical procedure. Further, there is a need for devices and methods that provide fine ablation capabilities of nerve and/or soft tissue. Devices and methods that assist in the control of necrosis in a tissue being treated are also needed.

SUMMARY

Ablation devices and methods are provided that allow accurate and efficient ablation of nerve and/or soft tissue. The device allows imaging of the ablation site and then uses a probe and/or bone piercing instrument that comprises an LED (light emitting diode) sensor to assist with accurate and precise ablation. The ablation devices and methods provided allow a passage to be made at a surgical site using an LED sensor navigated bone piercing instrument. In some embodiments, a proximal end of an ablation probe comprising an LED sensor is then easily navigated through the passageway to access an optimal location for ablation. In some embodiments, the LED sensor is attached to a camera system to triangulate the position of the probe and/or bone piercing instrument relative to a patient's anatomy. In various embodiments, the geometric shape of the probe and/or bone fastener is predefined so that a computer can calculate where a tip of the probe and/or bone fastener is within the patient's body. In some embodiments, the devices and methods provided are reusable for multiple procedures and are antimicrobial. In some embodiments, the devices and methods provided are not reusable. In some embodiments, the ablation probe and bone piercing instrument both contain an LED sensor.

In some embodiments, the ablation devices, methods and kits provided allow ablation of nerves and other soft tissue via a minimally invasive procedure to alleviate pain. The ablation devices, methods and kits disclosed comprise a probe having an exterior and an interior. The exterior comprises a tip and the interior defines a passage having a filament. The filament has an opening configured to release a pressurized material into the interior of the probe so as to cool the tip to a selected temperature to ablate nerve and/or soft tissue. Optionally, a bone piercing instrument is provided that is configured to pierce bone so as to allow entry of the probe into the bone.

In some embodiments, an ablation kit comprises a probe having an exterior and an interior. The exterior comprises a tip and the interior defines a passage having a filament and insulation disposed therein. The filament has an opening configured to release a pressurized material into the interior of the probe so as to cool the tip to a selected temperature to ablate nerve and/or soft tissue. Optionally, a bone piercing instrument is provided that is configured to pierce bone so as to allow entry of the probe into the bone.

In certain embodiments, methods for destroying nerves and other soft tissue via a minimally invasive procedure to alleviate pain are also provided. Destroying the target nerve or soft tissue can eliminate and/or reduce pain symptoms. Specific clinical applications of the disclosed ablation instrument include destruction of nerves causing facet and discogenic back and leg pain, destruction of soft tissue causing stenosis pain symptoms, and many other orthopedic and oral maxillofacial pains, ENT pains and pathologies. Ablation will destroy cellular contents, but retain tissue architecture. The destroyed nerve will fill with scar tissue blocking nerve regrowth and conduction.

In some embodiments, a method of ablation is provided. The method comprises: creating a bone cavity with a bone piercing instrument having an LED sensor, the bone cavity being adjacent to the nerve and/or soft tissue; inserting a probe within the bone cavity, the probe having an exterior and an interior, the exterior comprising a tip and a proximal end comprising an LED sensor, and the interior having a passage comprising a filament, the filament having an opening configured to release a pressurized material into the interior of the probe so as to cool the tip to a selected temperature to ablate nerve and/or soft tissue.

In some embodiments, a method of ablation is provided. The method comprises: creating a bone cavity with a bone piercing instrument having an LED sensor, the bone cavity being adjacent to the nerve and/or soft tissue; inserting an installation sleeve into the bone cavity to reduce tissue damage along a path of the bone cavity; and inserting a probe within the installation sleeve, the probe having an exterior and an interior, the exterior comprising a tip and a proximal end comprising an LED sensor, and the interior defining a passage containing a filament, the filament having an opening configured to release a pressurized material into the interior of the probe so as to cool the tip to a selected temperature to ablate nerve and/or soft tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
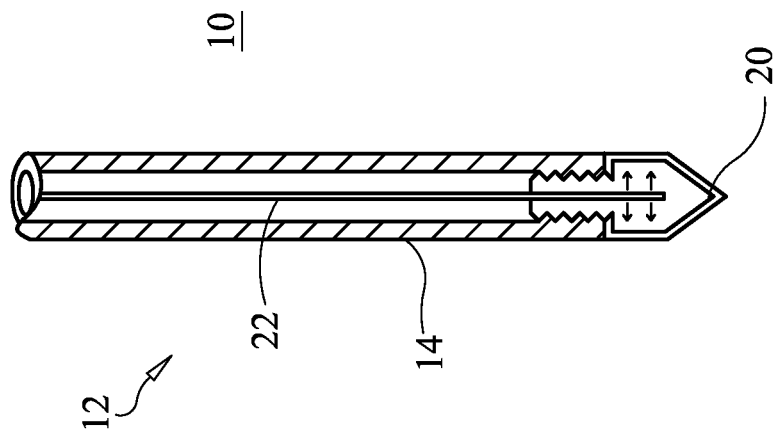
FIGS. 1 and 1A illustrates a cross sectional view of an ablation device in accordance with one embodiment of the present disclosure.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Devices for accurate and efficient ablation of nerve and/or soft tissue suitable for use in open surgical and/or minimally invasive procedures for the treatment of pain are disclosed. The following description is presented to enable any person skilled in the art to make and use the present disclosure. Descriptions of specific embodiments and applications are provided only as examples and various modifications will be readily apparent to those skilled in the art.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Definitions

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Cryoablation

Cryoablation devices have been available to surgeons to treat many medical conditions, for example, in the treatment of tumors in lung, liver, kidney and other body organs. Cryoablation has also been used for treatment of tumors, cardiac arrhythmias, chronic and post-operative pain, bone fracture and soft tissue wounds.

Cold temperatures have been used to decrease inflammation and to relieve pain since the ancient Egyptians. Liquid air and carbon dioxide were used to treat skin lesions in the beginning of the twentieth century. In 1950, liquid nitrogen was introduced into clinical practice for the cryosurgical ablation of a variety of skin diseases and allowed for deeper tissue to be treated with cryoablation. In 1961, a liquid nitrogen probe was developed and was used to treat Parkinson's disease as well as inoperable brain tumors. From 1980-2000, systems emerged based on an advanced gas expansion method known as the Joule-Thomson Principle. This principle allows for temperature change of a gas or liquid when it is forced through a valve or porous plug while being kept insulated so that no heat is exchanged with the environment. The refrigerant could be stored at room temperature and the difficulties associated with supplying liquid nitrogen to the operating room disappeared. Three main refrigerants were utilized: nitric oxide, liquid nitrogen and argon. For over 20 years, rigid cryoprobes have existed for percutaneous use or in open invasive surgical procedures. For example, cryoprobes are used for freezing a range of lesions from prostate tissue to metastatic cancers in liver. Neuronal tissue has been frozen with such devices for the relief of pain.

Current cryoablation procedures and techniques employ cryoprobes that utilize a needle that forms an ice ball centered around a tip disposed at a surgical site. Before the tip can be positioned into another area of the surgical site, a medical practitioner must wait for the ice ball to adequately melt before removal. Therefore, to ablate multiple areas of the surgical site, a considerable amount of time is wasted and the amount of time that it takes to perform a procedure is lengthened. Therefore, the probe of the present disclosure decreases the amount of time wasted during a surgical procedure for enhanced ablation. The cryoablation probes and/or bone piercing instrument comprise an LED sensor coupled to a computer tracking system that allow location and position to be determined for precise ablation. In some embodiments, imaging (CT, MRI) can be used in addition to the LED probe and/or LED bone piercing instrument.

Discogenic Pain

The devices and methods provided can be used to treat discogenic pain. Pain arising from the disc or elements adjacent to an intervertebral disc may cause axial pain also called discogenic pain with or without a radiculopathy component. Generally, though not always, to experience pain in a particular region the presence of nerve endings in that region is required. One source of pain is caused by the activation of specific nociceptors connected with C- and A-delta fibers. Another source of pain involves injury to sensory fibers, or damage to the central nervous system. Alternatively, abnormal interactions between neuronal extensions of sensory and autonomic nature can also be involved in symptomatic pain. Hence, the innervation of the disc and elements adjacent to an intervertebral disc is of interest to the study of discogenic pain.

Neuronal extensions innervating the disc and region adjacent to the disc are of motor, sensory or autonomic nature. Normal discs are rarely innervated deeper than the outer third of the annulus fibrosus. However, there are indications that degenerating or problematic discs have nerve extensions that extend centripetally beyond the outer third of the annulus fibrosis, reaching as far as the inner third of the annulus fibrosis, or even into the nucleus pulposus. The invasion of such neuronal extensions may be a source of pain, particularly if they come into contact with those substances in the nucleus pulposus that are capable of exciting such neuronal extensions. Signs of degeneration associated with the development of axial pain with or without radiculopathy such as increasing innervation have also been found in elements adjacent to the disc, for example the endplates.

Discs are generally avascular, with the transport of nutrients and metabolites occurring primarily through diffusion. However, degenerations tend to be more vascular than normal discs. This centripetally invasive vascularization of the disc, analogous to the neuronal invasion, may contain a perivascular nerve network with vasomotor or vasosensory functionalities. Further, increased vascularization of the disc is associated with increased innervation, and hence increased chances for discogenic pain.

The present disclosure incorporates LED navigation with both a probe and a bone piercing instrument into a device that is capable of efficiently ablating areas of a surgical site. The use of LED navigation, a probe and a bone piercing instrument in the present disclosure allows a surgical site to be quickly identified and treated. In some embodiments, the LED sensor of the probe and the LED sensor in the bone piercing instrument can send and receive signals to each other in conjunction with the computer tracking system to further enhance ablation (e.g., Medtronic Stealth navigation systems). These modules shown in FIG. 5, allow the system to send and receive data points for tracking and allow for precise ablation. Each LED sensor, in some embodiments, can have a timing module that allows for example, the LED sensor of the bone piercing instrument to turn off, and the system will signal the user to position the probe also having an LED sensor adjacent the nerve and/or soft tissue to be ablated.

As illustrated in FIGS. 1-5, the present ablation device 10 comprises a probe 12 (FIG. 1). The dimensions of the device, among other things, will depend on the site that needs ablation. For example, the width of the cervical facet is only about 0.5-1.0 cm and about 1.0-2.0 cm for the lumbar facet region. Thus, the device, in various embodiments, can be designed for these specific areas.

Some examples of lengths of the probe, may include, but are not limited to, from about 50 to 150 mm in length, for example, about 50 mm for the cervical facet use, about 100 mm for a lumbar facet use in a standard adult and about 150 mm for an obese adult patient. The thickness of the probe will depend on the site that needs ablation and/or the particular embodiment of the device. The thickness of the probe is about 20 gauge. In some embodiments, the probe can be about 17 to about 22 gauge. In various embodiments, the thickness includes, but is not limited to, from about 0.05 to about 1.655. In some embodiments the probe can be increasing and or decreasing in thickness throughout the probe. In some embodiments, the probe may be tapered and/or angled. The probe may be the widest or smallest diameter or a diameter in between for insertion into a human or animal body. In some embodiments, the widest diameter is typically about 14 gauge, while the smallest diameter is about 26 gauge.

Probe 12 comprising of an exterior surface 14 and an interior surface 16. The interior surface defines a passage 18. In some embodiments, probe 12 can have one or more passages defined by the interior surface for a pressurized material to be released into the probe as well as recirculation throughout the probe. Exterior surface 14 comprises a tip 20 positioned at a distal end of the probe. In various embodiments, the exterior surface is rough, smooth, dimpled and/or textured.

Figure 2:
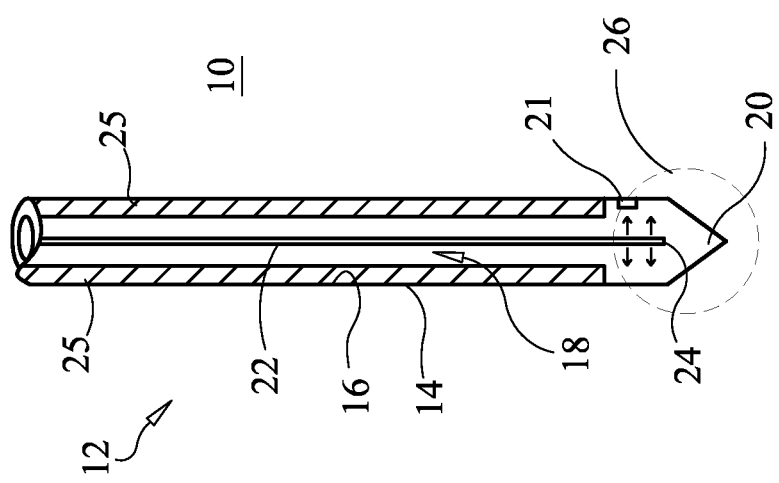
FIGS. 2 and 2A illustrates a cross section view of an ablation device in accordance with one embodiment of the present disclosure.
Figure 2A:
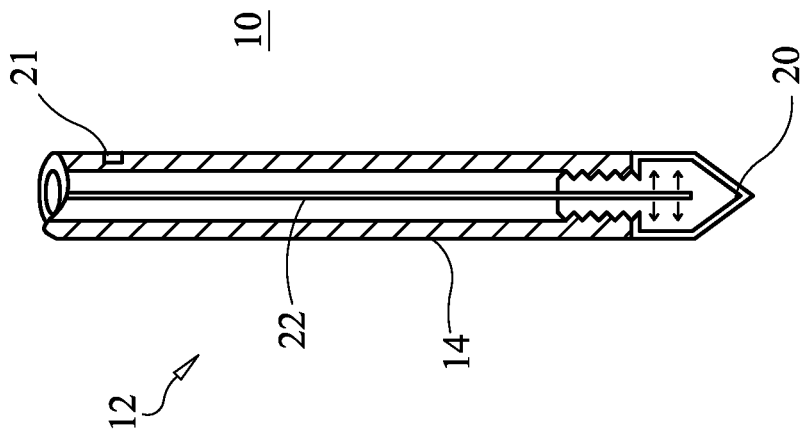

In some embodiments, tip 20 is blunt and is not configured to penetrate a surgical site and/or is not configured for creating a passageway into bone. In some embodiments, the tip of the probe can be round or tapered. In various embodiments, the tip is smooth for insertion. In some embodiments, the tip is detachable from the probe. In various embodiments, the probe and tip are configured for threaded, friction fit, ball and socket, clip, key/keyway and/or male/female engagement (FIG. 2). In some embodiments, the tip comprises a temperature conductive material comprising stainless steel, copper, silver, gold, aluminum, brass, platinum, molybdenum and/or tungsten.

In various embodiments, tip 20 can include at least one opening to inject material into a surgical site to facilitate ice ball formation. The openings may be shaped as a regular or irregular polygon including arcuate, round, square, oblong, kidney shaped, crescent, or beveled shaped. In some embodiments, therapeutic agents can be delivered to the surgical site via the at least one opening.

In some embodiments, the tip comprises a navigation sensor, such as for example, an LED sensor 21 that is coupled to a monitoring device such as, for example, as computer system 23 (FIG. 5) to track the location of the tip within a surgical site, such as, for example, a bone cavity. In various embodiments, a monitoring device, an imaging device(s), and a display unit are incorporated into sensor navigation. The operation of the probe and the bone piercing instrument is controlled by the monitoring device, which is connected to an ablation device. The monitoring device comprises at least a temperature sensor (e.g., a thermocouple), at least a pressure sensor, and at least a position sensor. In various embodiments, the monitoring device may include or be coupled to a computer processor that executes instructions to provide the function of the monitoring device; a display unit connected to the computer processor and provide imaging information associated with an ablation procedure (e.g., from an imaging device); display pressure, temperature, time information (e.g., elapsed time since a given phase of treatment was started) and probe position.

Figure 5:
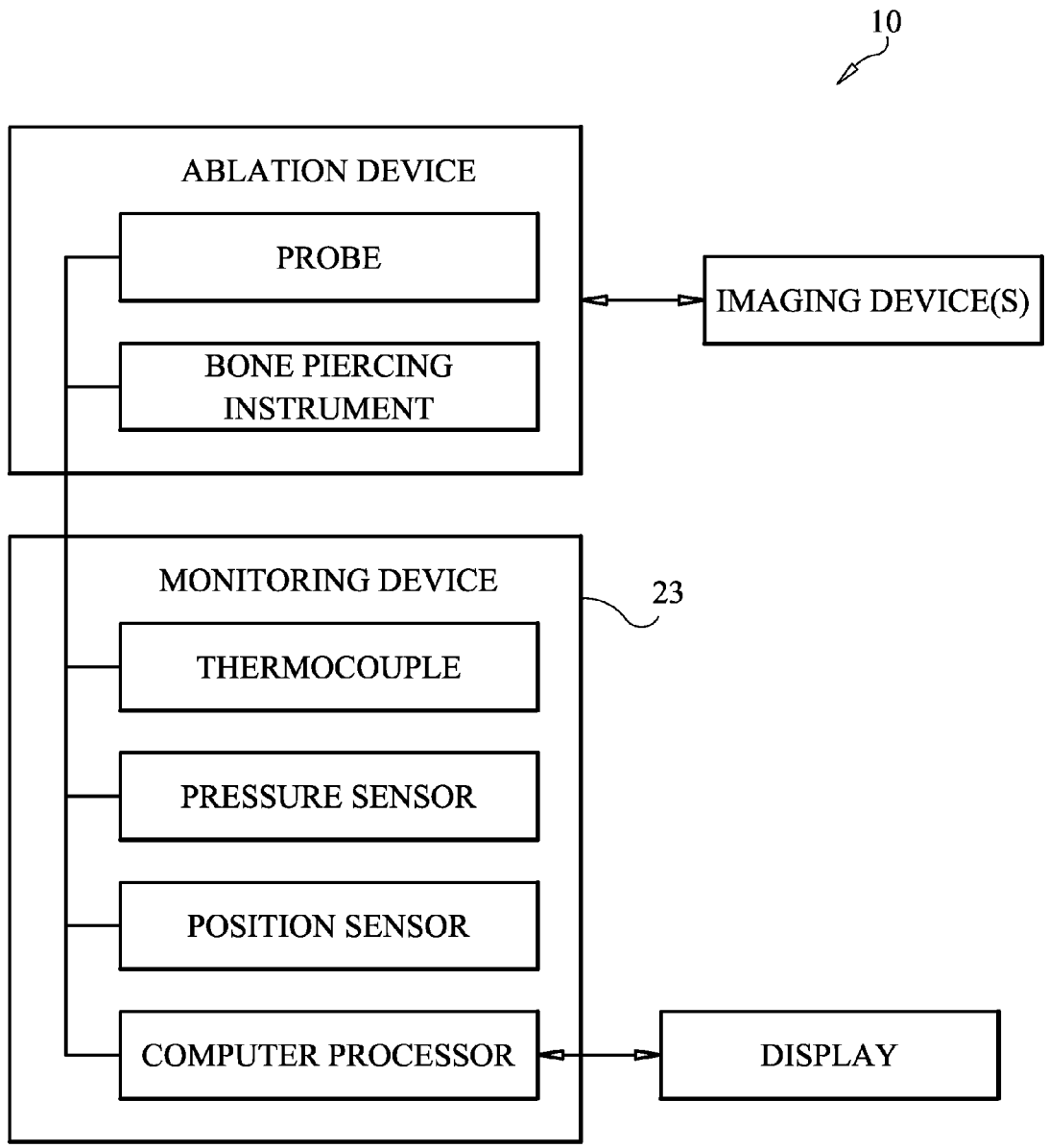
FIG. 5 illustrates a block diagram of an ablation system in accordance with one embodiment of the present disclosure.

The ablation probe, bone piercing instrument can be coupled to the computer system 23 in a wired or wireless fashion. These can also contain processors that execute instructions for navigation as well as other data needed to create and/or ablate a target site at or near nerve tissue and/or soft tissue. Although the components of FIG. 5 are shown as separate modules, it will be understood that they can be all part of one or more computer system(s).

Figure 1A:
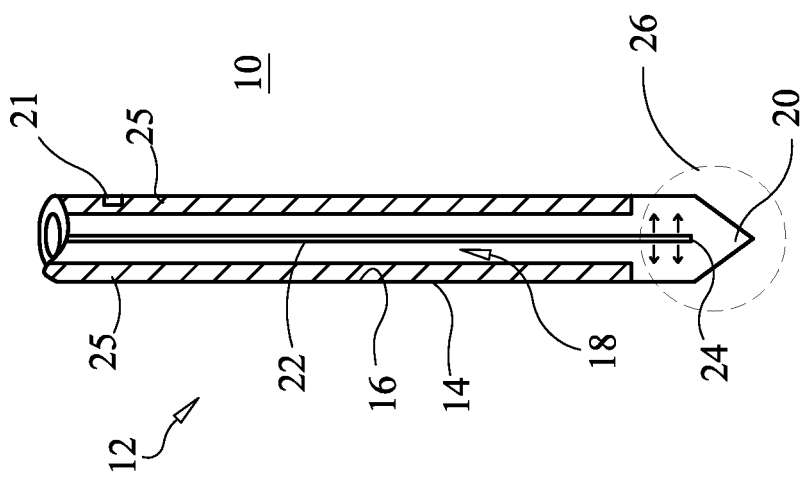
Figure 3:
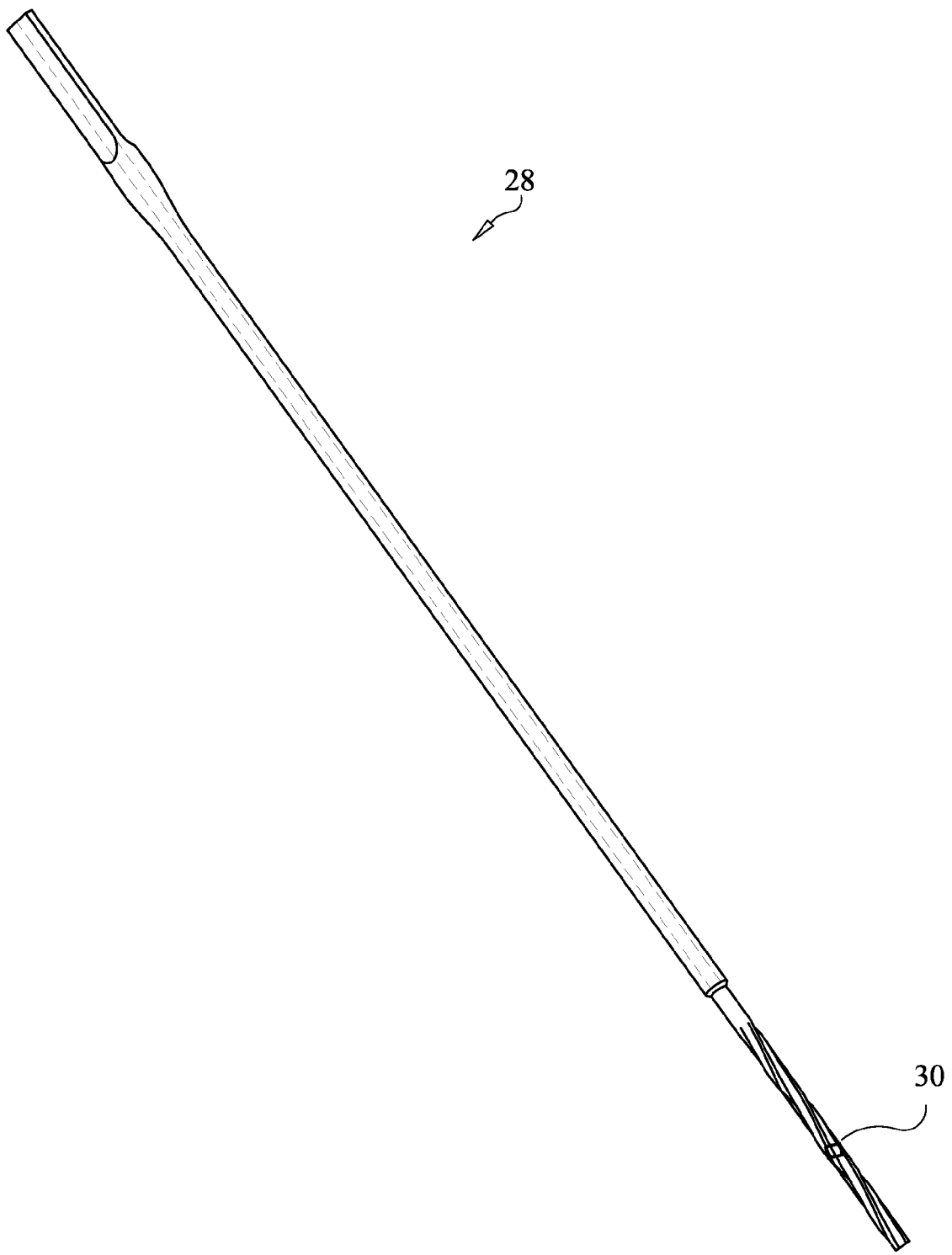
FIG. 3 illustrates a front view of an ablation device in accordance with one embodiment of the present disclosure.

In various embodiments, the LED sensor can be disposed on one side of the probe. In some embodiments, the LED sensor can be disposed at an end of the tip. In some embodiments, the LED sensor 21 is disposed at a proximal end of the probe (FIGS. 1A and 1B). In various embodiments, the LED sensor is disposed on a probe handle (not shown). In various embodiments, the navigation sensor comprises a battery, an electrode, a recharger, a transmitter, a receiver, a transceiver, a sensor, a recorder, a capacitor, a transformer, a system control unit, a programmer, an address/positioning unit, a temperature sensor, a temperature adjuster, a thermogenerator, a thermoelectric generator, a pressure sensor, a pressure adjuster, a mechanical power generator, a photo/light generator, an ultraviolet light generator, an infrared generator, an optical stimulator, a laser, a radiofrequency generator, a magnetic field generator, a mechanical vibration generator, an ultrasonic wave generator, an electrical field generator, a radiation generator or a fuel cell. The LED sensor, in some embodiments, has a communication module that allows communication between the computer system and any LED sensor of the bone piercing instrument. In some embodiments, the LED sensor of the probe can have a temperature sensor that can sense temperature and sends this information to the computer system for display.

In various embodiments, monitoring devices may be used that comprise sensors that may receive and record data relating to temperature, light, density, impedance, and position of an ablation probe in the form of radiowaves, microwaves, spectroscopy, and the like.

In some embodiments, a filament 22 is disposed within the passage of the probe. The filament is about 0.016 inches in diameter. In some embodiments, the filament is about 0.010 to 0.015 or about 0.17 to about 0.25 inches in diameter. The filament is a conduit for cooling and expansion of the pressurized material that is released and passed into the probe.

The filament includes an opening 24 configured to release the pressurized material into the interior surface of the probe. The opening may be shaped as a regular or irregular polygon including arcuate, round, square, oblong, kidney shaped, crescent, or beveled shaped. The pressurized material is released and enters into the passage cooling and expanding within the passage via the filament.

The material is pressurized and in some embodiments, the pressure is from about 3,000 to about 6,000 pounds per square inch (PSI). In various embodiments, the material is in the form of argon, liquid nitrogen, nitric oxide, helium, air, krypton, carbon dioxide, tetrafluoromethane or xenon. When a high pressure material such as argon is used, argon will expand within the interior and form a cryogenic pool at the tip, cooling the surface of the tip. The temperature of the material is coldest at the tip of probe 12. In one embodiment, tip 20 is made of a heat conducting material such as metal so as to enable the formation of an ice ball 26. The ice ball is spherical or oval in shape.

In various embodiments, the interior surface of the probe comprises insulation 25. In some embodiments, the insulation is configured to prevent the probe from damaging adjacent tissues at a surgical site. The insulation includes, but is not limited to a cavity, sheet, film, layer or coating comprising a gas, fluid, glass, ceramic, plastic, rubber or porcelain. In various embodiments, the insulation does not cover an interior surface of the tip. In various embodiments, the insulation has varying thickness throughout. In some embodiments, the thickness of the insulation can be from about 0.01 to about 0.3 inches.

Suitable materials that probe 12 can be made from for example are, polyurethane, polyurea, polyether(amide), PEBA, thermoplastic elastomeric olefin, copolyester, and styrenic thermoplastic elastomer, steel, aluminum, stainless steel, titanium, nitinol, tungsten, molybdenum, metal alloys with high non-ferrous metal content and a low relative proportion of iron, carbon fiber, glass fiber, plastics, ceramics or a combination thereof.

Device 10 includes a bone piercing instrument 28 (FIG. 3) configured to pierce a surgical site, such as, for example, bone and to create a bone cavity 29 (FIG. 4) for disposal of the probe tip. In various embodiments, the bone piercing instrument is a drill, pin, bone tap, awl, Steinmann pin or Steinmann drill. Some examples of lengths of the bone piercing instrument, include, but are not limited to, from about 12 to about 300 mm in length, depending on the surgical site, the patient's age and/or weight. The thickness of the bone piercing instrument will depend on the site that needs ablation and/or the particular embodiment of the device. The thickness of the bone piercing instrument is from about 2 to about 12 mm. In some embodiments, the thickness of the bone piercing instrument can be about 4 to about 8 mm. In some embodiments the bone piercing instrument can be increasing and or decreasing in thickness throughout. In some embodiments, the bone piercing instrument may be tapered and/or angled. The bone piercing instrument may be the widest or smallest diameter or a diameter in between for insertion into a human or animal body. In some embodiments, the widest diameter is typically about 12 gauge, while the smallest diameter is about 2 gauge. In various embodiments, the diameter can be 2, 3, 4, 5, 6, 7, 8, 9, 10, 11 and/or 12 mm.

In some embodiments, the depth of bone that the bone piercing instrument can pierce includes for example, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 30 mm, 40 mm or 50 mm.

In some embodiments, the bone piercing instrument comprises a navigation sensor, such as, for example an LED sensor 30 disposed at a distal end of the bone piercing instrument. In various embodiments, the LED sensor is disposed on a proximal end of the bone piercing instrument. The LED sensor is coupled to the computer system and is configured to track the location of the bone piercing element within the bone cavity. It can be used to navigate at or near the ablation site because, in some embodiments, the LED sensor comprises a navigation module that allows tracking of the instrument about the body. In various embodiments, the navigation module comprises a battery, an electrode, a recharger, a transmitter, a receiver, a transceiver, a sensor, a recorder, a capacitor, a transformer, a system control unit, a programmer, an address/positioning unit, a temperature sensor, a temperature adjuster, a thermogenerator, a thermoelectric generator, a pressure sensor, a pressure adjuster, a mechanical power generator, a photo/light generator, an ultraviolet light generator, an infrared generator, an optical stimulator, a laser, a radiofrequency generator, a magnetic field generator, a mechanical vibration generator, an ultrasonic wave generator, an electrical field generator, a radiation generator or a fuel cell.

In some embodiments, the LED sensor of the bone piercing instrument can also indicate pressure and torque of the bone piercing instrument. This data can be sent back to the computer system and displayed to the user. Alternatively, there can be a timer feature that allows the bone piercing instrument to be turned off so that signals will only come from the ablation probe and not the bone piercing instrument.

In various embodiments, the bone piercing instrument may be fenestrated. In some embodiments, the bone piercing instrument may be canulated to allow for a material such as, for example, a therapeutic agent to be injected into the surgical site.

Figure 4:
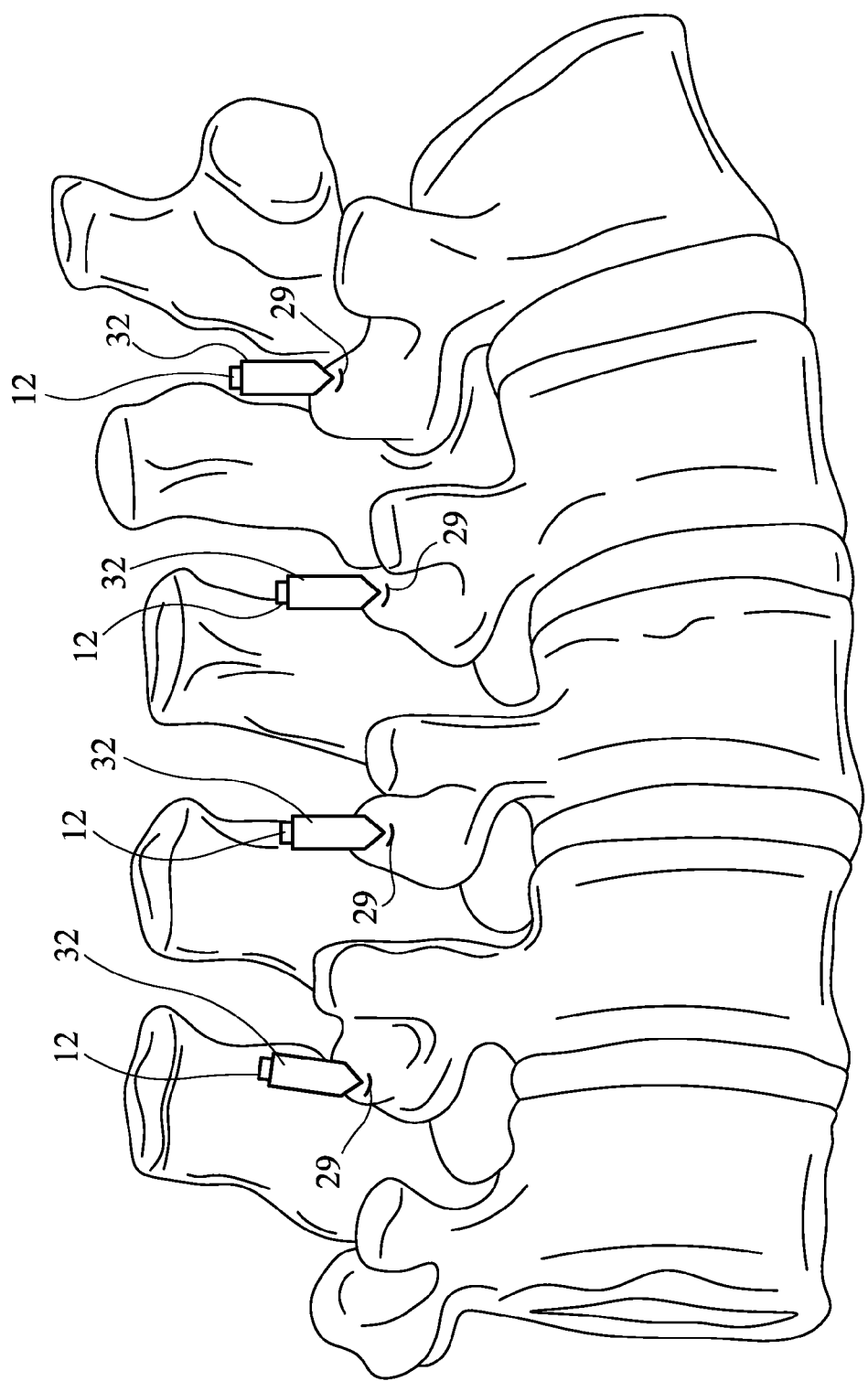
FIG. 4 illustrates a front view of an ablation device in accordance with one embodiment of the present disclosure disposed with vertebrae.

In various embodiments, device 10 includes an installation sleeve 32 (FIG. 4). The installation sleeve is configured for disposal within the bone cavity and to protect adjacent tissues at a surgical site from being damaged. In some embodiments, the installation sleeve does not cover the probe tip. In some embodiments, the installation sleeve is insulated and comprises a glass, ceramic, plastic, rubber and/or porcelain. In some embodiments, an outer surface of the installation sleeve comprises a viewing window (not show) configured to show probe translation within the sleeve. In various embodiments, the viewing window may be variously shaped, such as, for example, round, square, oblong, triangular, oval and/or polygonal. The viewing window can be offset on the outer surface of the installation sleeve.

In some embodiments, a lubricant is provided to assist in the insertion of tip 20 within the nerve and/or soft tissue. In some embodiments, the lubricant can be, without limitation, polyethylene glycol (PEG), hyaluronic acid, hyaluronan, lubricin, polyethylene glycol, and any combinations thereof.

After a period of time, ice ball 26 forms and begins to ablate when the tip of the probe is adjacent to nerve and/or soft tissue and when the temperature at the tip decreases from about −40° C. to about −160° C. The temperature at the surface of the ice ball is 0° C. The temperature declines exponentially towards a cool center where it reaches about −170° C. The ice ball will be formed at about 2 to about 8 minutes after the material has been released into probe 12. The sphere of the ice ball creates a zone of complete ablation (about −20° C.) typically located within the ice ball at approximately half way between the center of the ball and its outer surface. In various embodiments, nerve and or soft tissue is completely ablated in about 3 to 16 minutes. In some embodiments, the nerve and/or soft tissue is ablated in about 5 to 9 minutes. In some embodiments, the ice ball is not a complete ice ball, for example, a partial or half an ice ball can be formed for complete ablation.

The temperature for cryoablation of the device can be selected by the user and can vary as needed. For example, the temperature that can be selected can be from −180° C., −170° C., 160° C., −150° C., −140° C., −130° C., −120° C., −110° C., −100° C., −50° C., −40° C., −30° C., −20° C., −10° C., −5° C. or to about 0° C. or any temperature in between these numbers.

In some embodiments, a heated material can pass through the passage of the probe to heat the pressurized material thereby increasing temperature.

In various embodiments, the device is coated with an antimicrobial coating and/or agents. The antimicrobial coating can include, for example, antibiotics, antifungal, antiviral agents or the like. Antimicrobial agents to treat infection include by way of example and not limitation, antiseptic agents, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Some exemplary antimicrobial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefinenoxime hydrochloride; cefinetazole; cefinetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In some embodiments, the device can be coated with an antiviral agent. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Depending on the particular embodiment, the size of the probe tip determines the size of the ice ball formed. In some embodiments, the length of the tip is about 0.5 to about 2 mm for smaller ice balls and from about 3 to about 6 mm for larger ice balls.

In various embodiments, the tip of device 10 comprises a telescopic configuration. The tip can be manually or electronically movable so as to place the tip into a particular position within a surgical site. In certain embodiments, all or some of the tip comprise a telescopic configuration. In some embodiments, the tip is a navigational tool used to guide device 10 into a surgical site.

In some embodiments, the tip and/or bone piercing instrument of device 10 comprises indicia, for example a depth indicator that may include an analog, such as, for example, a dial with a numerical indicator of angle and/or digital display, such as, for example, LED and/or LCD. The graduations may represent various indicia, such as, for example, numerical, alphabetic and/or specific conditions/orientations, such as, initial depth and/or final depth of penetration into the nerve and/or tissue.

In certain embodiments, device 10 may include switches for manually controlling the operation of device 10 by a medical practitioner. The switches can provide functions such as on/off, cooling, and predetermined cycles of heating and cooling by selectively and controllably communicating device 10 with an external material container.

In some embodiments, different monitors of temperature, gas pressure and location on device 10 can be attached to device 10. In some embodiments, thermal sensors may be used for measuring the temperature of the material, the tip and/or the bone piercing instrument. In some embodiments, device 10 can be operatively connected to semi-steerable or navigational sources for easier guidance into tissues. In various embodiments, the navigational sources can be coupled with a pre-procedure such as for example, CT, MRI, PET scan, etc. so that the target nerve or soft tissue to be ablated can be identified and accurately located during the procedure.

In some embodiments, device 10 is attached to a pressure source that is configured to supply the pressurized material described above. In some embodiments, without limitation, the pressure source can be a pump, a cannula and or a catheter.

In various embodiment, at a proximal end, device 10 can be operatively connected to a vacuum (not shown) for providing suction to ablated nerve and/or tissue. The vacuum may be used to transmit vacuum from a vacuum source (not shown) to a receiving aperture (not shown) connected to device 10. Any suitable aspirator, cylindrical or otherwise, or other mechanism that creates vacuum upon the movement of an actuating member thereof, may be utilized as a vacuum source. The vacuum can be in communication with the tip of device 10 for providing suction to remove ablated nerve and/or soft tissue.

With further reference to FIGS. 1-2, not shown is an overall glass or other insulating layer covering most of the structure. In some embodiments, the coating or insulating layer can be glass or ceramic having a thickness from about 0.005 to about 0.5 mm thick or from about 0.01 to about 0.2 mm thick.

The glass type insulation is typically applied by a conventional process of dipping each relevant component prior to assembly in liquid (molten) glass and then annealing the glass. In some embodiments, the coating or insulation layer does not cover the entire probe. In some embodiments, the coating or insulation layer does cover the entire probe.

In various embodiments, the device may include radiographic markers to help indicate position on imaging procedures (e.g., CT scan, X-ray, fluoroscopy, PET scan, etc.). These may be disposed on or a portion of the device and include, but are not limited to, barium, calcium phosphate, and/or metal beads.

In some embodiments, device 10 can also have a blunt a probe tip. As a result, the surgeon or health practitioner can eliminate any difficulty in positioning the tips in the optimal location to get an optimal and consistent clinical result. The use of device 10 also results in avoiding necrosis of adjacent tissue, which can lead to clinical adverse events and requires these adjacent tissues to have to repair themselves. Positioning of the tip allows cryoablation to be applied near the tip and avoids hemisphere spacing around the tip to avoid unwanted necrosis.

In some embodiments, the probe tip and/or the bone piercing instrument can comprise grooves (not shown). Grooves can have edges shaped as a regular or irregular polygon including arcuate, round, square, oblong, oval, kidney shaped, beveled, or crescent shaped. The grooves can also include ridges or have no ridges. In various embodiments, the grooves are located at the tip and/or the distal end of the bone piercing instrument and can be closed when device 10 is inactive as device 10 is inserted towards the desired location. Once the nerve or soft tissue to resect is reached, grooves open, the material becomes activated to ablate the nerve or tissue protruding into each groove as device 10 is manually pushed into it.

In certain embodiments, device 10 can be provided with a tube or small channel (not shown) configured to deliver at the location of the severed nerve and/or soft tissue cement or polymer which can provide a physical barrier to prevent the temporary or permanent re-growth of nerve and/or soft tissue so that the pain symptoms do not return. This channel can be adjacent to the passage of the probe and can run parallel to the passage such that the device can ablate and deliver a therapeutic material or barrier (e.g., polymer, cement, gel, etc.) to the area after ablating it.

Methods for Ablation

The present disclosure also provides methods for destroying nerve and/or soft tissue. The methods comprise creating a bone cavity with a bone piercing instrument having an LED sensor, the bone cavity being adjacent to the nerve and/or soft tissue; inserting a probe within the bone cavity, the probe having an exterior and an interior, the exterior comprising a tip and a proximal end comprising an LED sensor, and the interior having a passage comprising a filament, the filament having an opening configured to release a pressurized material into the interior of the probe so as to cool the tip to a selected temperature to ablate nerve and/or soft tissue.

In some embodiments, the method of ablating nerve and/or soft tissue comprises: creating a bone cavity with a bone piercing instrument having an LED sensor, the bone cavity being adjacent to the nerve and/or soft tissue; inserting an installation sleeve into the bone cavity to reduce tissue damage along a path of the bone cavity; and inserting a probe within the installation sleeve, the probe having an exterior and an interior, the exterior comprising a tip and a proximal end comprising an LED sensor, and the interior defining a passage containing a filament, the filament having an opening configured to release a pressurized material into the interior of the probe so as to cool the tip to a selected temperature to ablate nerve and/or soft tissue.

In various embodiments, the ice ball forms at about 2-8 minutes and the nerve is ablated in about 3 to 16 minutes.

In other embodiments, the methods of the present disclosure further include delivering cement and/or a polymer through a small channel, for injection at the site of the nerve and/or soft tissue destruction to provide a physically barrier at the location of the nerve destruction to prevent temporary or permanent nerve regrowth, repair and return of the pain symptoms.

The barrier material utilized can be any suitable material effective to prevent or at least substantially inhibit the migration of substances that regrow tissue. Illustratively the barrier material can comprise a biodegradable synthetic polymer, in either flowable (and potentially hardenable) or non-flowable form. Illustratively, preferred barrier materials can have a first relatively flowable state during delivery and a second relatively less flowable state after implantation. For example, the barrier material may remain in an uncured, deformable, or otherwise configurable state during introduction, and rapidly cure, become harder or solidify after being introduced. Suitable materials that may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. In some embodiments, the barrier material can be a cement.

In several embodiments, the methods disclosed herein include operatively coupling the device to a source of navigational capability to allow easier pushing through the tissues. In various embodiments, the methods of ablation disclosed herein can include a pre-procedure step wherein the device can be coupled to a CT or MRI machine so that the target nerve and/or soft tissue to be ablated can be identified and accurately located during the destruction procedure.

The methods for ablation described hereinabove allow complete destruction of the nerve avoiding the problems and partial effectiveness of current cryoablation and RF devices available in the art, and also allow for more complete removal of soft tissue that is causing stenosis pain symptoms.

In various embodiments, kits are provided that include device 10. The kits can include at least one probe and at least one bone piercing instrument. In some embodiments, the probe and/or the bone piercing instrument is made reusable for multiple procedures after cleaning and sterilization.

Specific clinical application of this instrument include destruction of nerves causing facet and discogenic back and leg pain, destruction of soft tissue causing stenosis pain symptoms, and many other orthopedic and oral maxillofacial pain. Many other painful conditions associated with arthroscopic, otolaryngological or spinal procedures could use the ablation devices and methods of using these ablation devices described herein.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A cryoablation device comprising: a probe having an exterior and an interior, the exterior comprising a tip and the interior defining a passage having a filament and insulation disposed therein, the filament configured to conduct a pressurized material at a temperature from −180° C. to about 0° C. and having an opening configured to release the pressurized material into the interior of the probe so as to cool the tip to a selected temperature to ablate nerve and/or soft tissue; and a bone piercing instrument, the bone piercing instrument configured to pierce bone so as to allow entry of the probe into the bone, and a pressure of the pressurized material is from about 3,000 to about 6,000 pounds per square inch (PSI).

2. A device of claim 1, wherein the device is used to treat pain comprising discogenic pain.

3. A device of claim 1, wherein the bone piercing instrument creates a bone cavity configured for disposal of the probe therein and ablating nerve and/or soft tissue adjacent to the bone cavity.

4. A device of claim 3, wherein (i) the probe comprises a proximal end comprising an LED sensor, wherein the LED sensor is coupled to a computer to track the location of the tip within the bone cavity or (ii) the probe comprises a handle comprising an LED sensor, wherein the LED sensor is coupled to a computer to track the location of the tip within the bone cavity.

5. A device of claim 3, wherein the bone piercing instrument comprises an LED sensor coupled to a computer configured to track the location of the bone piercing instrument within the bone.

6. A device of claim 1, wherein the tip is blunt and comprises a temperature conductive material comprising stainless steel, copper, silver, gold, aluminum, brass, platinum, molybdenum or tungsten.

7. A device of claim 1, wherein the insulation is a layer or coating comprising, glass, ceramic, plastic, rubber or porcelain.

8. A device of claim 1, further comprising an installation sleeve configured for disposal within the bone cavity.

9. A device of claim 1, wherein the probe and the bone piercing instrument each comprise an LED sensor.

10. A method of ablating nerve and/or soft tissue, the method comprising: creating a bone cavity with a bone piercing instrument having an LED sensor, the bone cavity being adjacent to the nerve and/or soft tissue; inserting a probe within the bone cavity, the probe having an exterior and an interior, the exterior comprising a tip and a proximal end comprising an LED sensor, and the interior having a passage comprising a filament configured to conduct a pressurized material at a temperature from −180° C. to about 0° C. and having an opening configured to release the pressurized material into the interior of the probe so as to cool the tip to a selected temperature to form an ice ball within 2 to about 8 minutes to ablate nerve and/or soft tissue, and a pressure of the pressurized material is from about 3,000 to about 6,000 pounds per square inch (PSI).

11. A method of claim 9, wherein the nerve and/or soft tissue is ablated to treat pain comprising discogenic pain.

12. A method of claim 9, wherein the bone piercing instrument comprises an LED sensor coupled to a computer configured to track the location of the bone piercing instrument within the bone.

13. A method of claim 9, wherein the LED sensor is coupled to a computer to track the location of the tip within the bone cavity.

14. A method of claim 9, wherein the passage comprises an insulation comprising a layer or coating comprising, glass, ceramic, plastic, rubber or porcelain.

15. A method of claim 9, wherein an installation sleeve is configured for disposal within the bone cavity.

16. A method of claim 9, wherein a navigation device comprising a CT or MRI is used before the bone cavity is created to locate a selected nerve and/or soft tissue for ablation.

17. A method of ablating nerve and/or soft tissue, the method comprising:
creating a bone cavity with a bone piercing instrument having an LED sensor, the bone cavity being adjacent to the nerve and/or soft tissue; inserting an installation sleeve into the bone cavity to reduce tissue damage along a path of the bone cavity; and inserting a probe within the installation sleeve, the probe having an exterior and an interior, the exterior comprising a tip and a proximal end comprising an LED sensor, and the interior defining a passage containing a filament configured to conduct a pressurized material at a temperature from −180° C. to about 0° C. and having an opening configured to release a pressurized material into the interior of the probe so as to cool the tip to a selected temperature to form an ice ball within 2 to about 8 minutes to ablate nerve and/or soft tissue, and a pressure of the pressurized material is from about 3,000 to about 6,000 pounds per square inch (PSI).

18. A method of claim 17, wherein the bone piercing instrument comprises an LED sensor coupled to a computer configured to track the location of the bone piercing instrument within the bone.

19. A method of claim 17, wherein the LED sensor is coupled with a computer to track the location of the tip within the bone cavity.

20. A device of claim 1, wherein the tip has an LED sensor comprising a temperature sensor and a pressure sensor, and the insulation of the probe comprises a thickness from about 0.01 to about 0.3 inches, and the tip is telescopic.

* * * * *